US00PP34793P2

(12) United States Plant Patent
Espin

(10) Patent No.: US PP34,793 P2
(45) Date of Patent: Dec. 6, 2022

(54) GRAPEVINE PLANT NAMED 'GENSEL 3'

(50) Latin Name: *Vitis vinifera*
Varietal Denomination: GENSEL 3

(71) Applicant: Special New Fruit Licensing Mediterráneo S.L. (SNFL Mediterráneo S.L.), Murcia (ES)

(72) Inventor: Juan Carreño Espin, Murcia (ES)

(73) Assignee: Special New Fruit Licensing Mediterráneo S.L. (SNFL Mediterráneo S.L.), Murica (ES)

( * ) Notice: Subject to any disclaimer, the term of this patent is extended or adjusted under 35 U.S.C. 154(b) by 0 days.

(21) Appl. No.: 17/576,287

(22) Filed: Jan. 14, 2022

(51) Int. Cl.
*A01H 5/08* (2018.01)
*A01H 6/88* (2018.01)

(52) U.S. Cl.
USPC ..... Plt./205

(58) Field of Classification Search
USPC ..... Plt./205
CPC ..... A01H 5/08; A01H 5/00; A01H 5/0812; A01H 5/02; A01H 6/88
See application file for complete search history.

(56) References Cited

U.S. PATENT DOCUMENTS

PP22,125 P2 * 9/2011 Van Kleinwee ..... A01H 5/02 Plt./328
PP23,125 P2 * 10/2012 Sheehan ..... A01H 6/88 Plt./205

OTHER PUBLICATIONS

Vitis International Variety Catalogue 2022, retrieved on Mar. 23, 2022 at file:///C:/Users/jhwu/Downloads/Passport%20data%20-%20VIVC%20prime%20name_SHEEGENE%2020.pdf, one page. (Year: 2022).*
U.S. Appl. No. 17/576,262, filed Jan. 14, 2022, Espin.
U.S. Appl. No. 17/576,280, filed Jan. 14, 2022, Espin.

* cited by examiner

*Primary Examiner* — June Hwu
(74) *Attorney, Agent, or Firm* — Dentons US LLP

(57) ABSTRACT

'GENSEL 3' is a new and distinct grapevine plant with novel characteristics that include good fertility and excellent fruity labrusca flavor. The berries produced by 'GENSEL 3' are reddish black and seedless with a crisp texture and no detectable seed traces. The berries produced by 'GENSEL 3' are large, weighing 9 g/berry on average, and harvested at the beginning of August until the end of September in Murcia Region (Spain).

1 Drawing Sheet

Latin name of the genus and species of the plant claimed: *Vitis vinifera.*

Cultivar denomination: 'GENSEL 3'.

BACKGROUND OF THE INVENTION

The present invention relates to a new distinct variety of seedless grapevine named 'GENSEL 3'. The new variety originated from a hybridization performed in Murcia, Spain during 2015 between '550P-2010' (not patented), as the pollen parent, and '9-704' (U.S. Plant Pat. No. 23,125), as the seed parent. Abortive seed traces were embryo cultured and the resulting plant was planted in an evaluation block during 2016. The first evaluation of the fruit produced by 'GENSEL 3' was performed during 2017. 'GENSEL 3' was first asexually propagated by field grafting dormant hardwood scions to 1103 Paulsen Rootstock (not patented) in 2018 in Murcia, Spain. Fruit from the resulting four grafted 'GENSEL 3' vines was first harvested in 2019. All characteristics and distinctions remain true to form and are established and transmitted through succeeding propagations.

SUMMARY OF THE INVENTION

The following are the most outstanding and distinguishing characteristics of 'GENSEL 3'. 'GENSEL 3' produces naturally large (9 g/berry) seedless reddish black (5 RP3/2)

berries having a broad ellipsoid shape with an excellent fruity labrusca flavor, that are harvested from mid-August to mid-September, in Murcia-Spain.

'GENSEL 3' is believed to be most similar to 'Kyoho' (unpatented). Nonetheless, the new cultivar can be distinguished from 'Kyoho' based at least upon harvest period, seedlessness, berry texture and cluster compactness. 'GENSEL 3' matures from mid-August to mid-September whereas 'Kyoho' matures in August. The berries produced by 'GENSEL 3' are seedless whilst the berries produced by 'Kyoho' have seeds. 'GENSEL 3' produces berries with a very firm texture whilst the 'Kyoho' berries are soft. The new variety, 'GENSEL 3', has tight bunches whereas the bunches of 'Kyoho' have a loose compactness.

'GENSEL 3' can be distinguished from its male parent, '550P-2010', in that the new cultivar is harvested from mid-August to mid-September whilst the harvest time of '550P-2010' is in end of July. 'GENSEL 3' clusters are heavier than '550P-2010' clusters (average 550 g v. 300 g). The berries of 'GENSEL 3' are larger than the berries of '550P-2010' (average 23.4 mm v. 15 mm). The berries of 'GENSEL 3' have a very firm texture whereas the berries of '550P-2010' are soft.

'GENSEL 3' can be distinguished from its female parent, '9-704', in that the berries of 'GENSEL 3' have a broad ellipsoid shape whereas the berries of '9-704' have an oval shape. The berries of 'GENSEL 3' have an excellent fruity labrusca flavor while the berries of '9-704' have a neutral flavor. The bunches of 'GENSEL 3' are tight whilst the bunches of '9-704' have a medium compactness. The harvest time of 'GENSEL 3' is from mid-August to mid-September whilst the harvest time of '9-704' is in early October. The new variety, 'GENSEL 3', has a lower fertility rate than '9-704' (1.2 v. 1.4).

BRIEF DESCRIPTION OF THE DRAWING

FIG. 1—Shows the form, foliage, and fruit of a 4-year-old 'GENSEL 3' vine grown in the field at Murcia, Spain. The colors shown are as true as can be reasonably obtained by conventional photographic procedures.

DETAILED BOTANICAL DESCRIPTION

The following detailed description sets forth the distinctive characteristics of 'GENSEL 3'. The detailed description was obtained between March and November using 4-year-old plants grown in the field in Murcia, Spain. The color references are to the Munsell Plant Tissue Color Book, 2012 Edition by Munsell Color.

Classification:
- *Family*.—Vitaceae.
- *Botanical.—Vitis vinifera.*
- *Common name*.—Grapevine.
- *Cultivar name*.—'GENSEL 3'.

Plant:
- *Plant habit and growth*.—Erect.
- *Age at maturity*.—4 years old.
- *Size* (*at maturity*).—Height: 225 cm. Width: 300 cm.
- *Vigor*.—Medium-high.
- *Productivity*.—Medium.
- *Rootstock*.—Name of rootstock: 1103 Paulsen Rootstock (not patented). Age of rootstock at time of grafting: one year old.

Trunk:
- *Size*.—Diameter: 4.5 cm. Height (at measured diameter of 4.5 cm): 45 cm above the ground.
- *Shape*.—Straight and cylindrical.
- *Surface texture*.—Smooth with the outer layer easily removed.
- *Bark color*.—Exterior 5YR4/2. Interior 5YR4/4.

Canes:
- *Size*.—Diameter: 10.4 mm. Length: 140.6 cm.
- *Surface texture*.—Mature cane: smooth and grained, with low density of postrate hairs on internodes. Inmature cane: smooth, finely ribbed, with low density of postrate hairs on internodes.
- *Form* (*woody shoot cross section form*).—Circular; pith in center with diaphragm at nodes.
- *Color*.—Mature: 5 months, 2.5GY5/8 (anthocyanins 10R4/4). Immature: 4 weeks, 5GY5/6 (anthocyanins 5YR3/4). Dorsal side of internodes: 5GY7/8; anthocyanins: 5R3/8. Ventral side of internodes: 5GY7/8. Dorsal side of nodes: 5GY7/8; anthocyanins:5R3/8. Ventral side of nodes: 5GY7/8.
- *Internode length* (*upper mature sun cane*).—7.24 cm.
- *Internode width*.—13.7 mm.

Bud:
- *Bud description*.—Winter bud: pointed and elongated, color 5YR4/4. Green bud: big, rounded and pointed, with anthocyanins (5R3/8).
- *Time of bud burst*.—25 February.
- *Time of bud leaf burst*.—3 March.

Tendrils:
- *Form*.—Mostly bifid.
- *Size*.—Medium.
- *Length*.—21.6 mm.
- *Diameter*.—3.2 mm.
- *Texture and distribution of tendril at each node beginning at base*.—Smooth, discontinuous, 00000000101010100101 01 (0 means no tendril at that node and 1 means there is tendril at the node).
- *Color*.—Mature: 4 weeks, 2.5GY6/8. Inmature: 10 days, 2.5GY5/6.
- *Anthocynanin*.—Mature: 5Y5/4. Immature: 7.5YR4/4.

Growing tips (young shoot):
- *Pubescence*.—Present, high density of prostate hair on the shoot tip.
- *Color*.—2.5GY6/8.
- *Anthocynanin*.—Absent.
- *Shape*.—Fully open.
- *Apex*.—Triangular.
- *Form of tip*.—Fully open.
- *Shoot attitude before tying*.—Erect.

Leaves:
- *Shape*.—Pentagonal.
- *Apex*.—Pointed.
- *Base*.—Rounded.
- *Number of lobes*.—5.
- *Depth of upper lateral sinuses of mature leaves*.—Very deep.
- *Arrangement of lobes of upper lateral sinuses on mature leaves*.—Slightly overlapped.
- *Margin*.—Irregular teeth.
- *Length of teeth on margin*.—2 to 10 mm.
- *Shape of teeth on margin*.—Both sides convex.
- *Texture* (*mature leaf*).—Upper surface: smooth and flat. Lower surface: smooth, with low density of prostrate hairs between main veins on lower side of blade.
- *Size*.—Immature: Length: 10 days, 7.8 cm. Width: 10 days, 7.6 cm. Mature: Length: 4 weeks, 17.7 cm. Width: 4 weeks, 15.9 cm. Ratio of length/width of teeth (mature leaf): small.
- *Color*.—Immature leaf: Upper surface: 5GY4/4, anthocyanins 5YR3/4. Proportion of main veins of the upper leaf with anthocyanin coloration: low (up to the first bifurcation). Lower surface: 5GY5/6. Mature leaf: Upper surface: 7.5GY4/4. Lower surface: 5GY5/4. Autumn coloration: Upper surface: 2.5Y8/8. Lower surface: 2.5Y7/6.
- *Venation*.—Pattern: palmate (veins on upper leaf are flat; veins on lower leaf are raised). Length of middle vein in mature leaves: 12.2 cm. Color: Upper surface: 2.5GY6/6. Lower surface: 5GY7/6.
- *Petiolar sinus*.—Slightly overlapped.
- *Petiole*.—Length: 10.7 cm. Diameter: 3.3 mm. Color: 5GY7/8, anthocyanins 5YR5/4.

Floral cluster:
- *General description and location*.—Mostly in the sixth node, range 5-7 nodes; 85% of clusters have shoulders.
- *Quantity of inflorescences per cluster*.—424.
- *Size*.—Length: 17.33 cm. Width: 10.3 cm spread; 7.5 cm hanging.
- *Peduncle*.—Length: 6.7 cm.
- *Inflorescences*.—Hermaphroditic.
- *Stamens*.—Straight, 1.7 mm.
- *Anthers*.—Small, nondescript.

*Date of bloom*.—Start: 24 April, 50%: 3 May, 100%: 9 May.

*Pollen amount*.—Sparse.

*Calyptra*.—5 segments, complete separation.

*Calyptra color*.—5GY5/6.

Fruit:

*Time of year of commercial harvest and shipment*.—August 15.

*Time of beginning of berry ripening*.—Medium to late.

*Keeping quality*.—After 30 days of refrigerated storage there are no symptoms of dehydration, the stems and berries are well preserved. The variety keeps its excellent and fruity flavor, as well as the crispness.

*Cluster* (*primary bunches*).—Generally size: large, 550 g. Length (without peduncle): 19.6 cm. Width: 12.3 cm hanging, 16.2 cm with shoulders spread. Density: tight. Peduncle length: 3.9 cm. Peduncle diameter: 5.6 cm. Peduncle color: 2.5GY 6/6. Number of berries per cluster: 64 (on average). Berry: Size: large, 9 g. Diameter: 23.4 mm. Length: 25.9 mm. Shape: broad ellipsoid. Uniformity: very uniform. Brix content: 20. Tiritable acidity: 0.57. Skin color (without bloom): 5RP3/2. Skin color (with bloom): 5R3/2. Pedicel: Length: 7.13 mm. Diameter: 2 mm. Color: 2.5GY6/6. Strength of attachment to berry: very strong, 10%.

*Cluster* (*secondary bunches*).—Generally size: small, 190 g. Length (without peduncle): 10.4 cm. Width: 8.5 cm hanging; 9.2 cm with shoulders spread. Density: tight. Peduncle length: 7.2 cm. Peduncle diameter: 3.4 mm. Peduncle color: 2.5GY6/6. Number of berries per cluster: 24 (on average). Berry: Size: medium, 6.3 g. Diameter: 21 mm. Length: 22 mm. Shape: broad ellipsoid. Uniformity: very uniform. Brix content: 20° Brix. Tiritable acidity: 0.56. Skin color (without bloom): 5RP3/2. Skin color (with bloom): 5R3/2. Pedicel: Length: 5 mm. Diameter: 2.7 mm. Color: 2.5GY6/6. Strength of attachment to berry: very strong, 10%.

Berry flesh:

*Color*.—2.5GY8/4.

*Juice, color*.—5Y7/4.

*Juice production*.—38%.

*Thickness of skin*.—Thick.

*Flavor*.—Excellent fruity labrusca flavor.

*Fragrance*.—Neutral.

*Texture*.—Juicy, firm.

*Seeds*.—Seed rudiments, non-detectable, average 1 per berry (color 5R3/6).

*Use*.—Table grape.

Disease and insect resistance: This cultivar is susceptible to the main diseases of its species, such as *Erysiphe necator, Plasmopara viticola, Botrytis cinerea, Daktulosphaira vitifoliae, Ceratitis capitata, Planococcus ficus, Planococcus citri, Empoasca vitis*.

What is claimed is:

1. A new and distinct variety of grapevine named 'GENSEL 3' as shown and described herein.

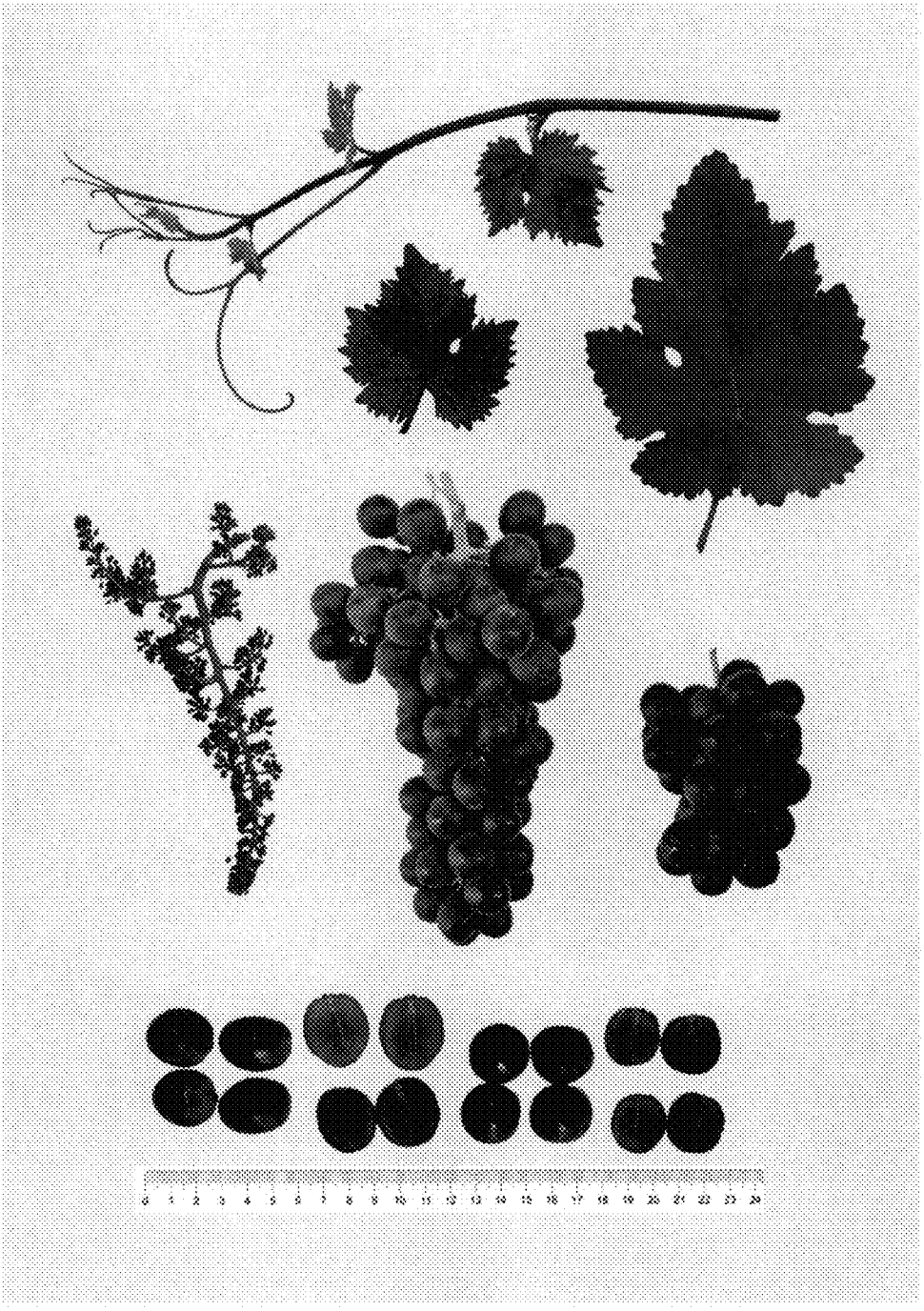

* * * * *